(12) United States Patent
Blanpied et al.

(10) Patent No.: US 6,506,812 B2
(45) Date of Patent: Jan. 14, 2003

(54) METHOD OF PRODUCING RIGID FOAMS AND PRODUCTS PRODUCED THEREFROM

(75) Inventors: Robert H. Blanpied; James Darryl Thornsberry, both of Meridian, MS (US); Steven E. Silverberg; James R. Lattner, both of Seabrook, TX (US); C. Harry McMullen, Kingwood, TX (US); Leonel E. Sanchez, League City, TX (US); Tronze-I Dennis Wu, Humble, TX (US)

(73) Assignee: Exxon Mobil Chemical Patents Inc, Houston, TX (US)

( * ) Notice: Subject to any disclaimer, the term of this patent is extended or adjusted under 35 U.S.C. 154(b) by 0 days.

(21) Appl. No.: 09/912,693

(22) Filed: Jul. 24, 2001

(65) Prior Publication Data

US 2002/0006978 A1 Jan. 17, 2002

Related U.S. Application Data

(63) Continuation of application No. 09/425,813, filed on Oct. 25, 1999, which is a continuation-in-part of application No. 08/498,276, filed on Jul. 3, 1995, now Pat. No. 5,578,652.
(60) Provisional application No. 60/024,031, filed on Aug. 6, 1996.

(51) Int. Cl.$^7$ .................................................. C08J 9/14
(52) U.S. Cl. ...................... 521/131; 521/125; 521/129; 521/172
(58) Field of Search .............................. 521/131, 172, 521/125, 129

(56) References Cited

U.S. PATENT DOCUMENTS

| | | | |
|---|---|---|---|
| 3,558,531 | A | 1/1971 | Salyer et al. |
| 3,993,609 | A | 11/1976 | Kamens et al. |
| 4,178,455 | A | 12/1979 | Hirai et al. |
| 4,636,529 | A | 1/1987 | Crooker |
| 4,721,823 | A | 1/1988 | Venier et al. |
| 4,898,893 | A | 2/1990 | Ashida |
| 4,927,863 | A | 5/1990 | Bartlett et al. |
| 4,929,782 | A | 5/1990 | Venier et al. |
| 4,981,876 | A | 1/1991 | Grimmer |
| 4,981,880 | A | 1/1991 | Lehmann et al. |
| 4,986,930 | A | 1/1991 | Lund et al. |
| 4,996,242 | A | 2/1991 | Lin |
| 5,032,623 | A | 7/1991 | Keske et al. |
| 5,070,113 | A | 12/1991 | Omure et al. |
| 5,096,933 | A | 3/1992 | Volkert |
| 5,114,986 | A | 5/1992 | Lin |
| 5,130,345 | A | 7/1992 | Li et al. |
| 5,166,182 | A | 11/1992 | Blanpied |
| 5,182,309 | A | 1/1993 | Hützen |
| 5,205,956 | A | 4/1993 | Volkert et al. |
| 5,213,707 | A | 5/1993 | Swan et al. |
| 5,227,088 | A | 7/1993 | Swan et al. |
| 5,234,967 | A | 8/1993 | Takezawa et al. |
| 5,236,611 | A | 8/1993 | Shiflett |
| 5,248,433 | A | 9/1993 | Felix et al. |
| 5,262,077 | A | 11/1993 | Bivens et al. |
| 5,277,834 | A | 1/1994 | Bivens et al. |
| 5,278,196 | A | 1/1994 | Robin et al. |
| 5,283,003 | A | 2/1994 | Chen |
| 5,290,823 | A | 3/1994 | Volkert |
| 5,296,516 | A | 3/1994 | Krueger et al. |
| 5,304,320 | A | 4/1994 | Barthélemy et al. |
| 5,314,926 | A | 5/1994 | Robin et al. |
| 5,318,996 | A | 6/1994 | Yu-Hallada et al. |
| 5,336,696 | A | 8/1994 | Ashida |
| 5,578,652 | A | * 11/1996 | Blampied et al. |
| 5,847,018 | A | * 12/1998 | Blampied et al. |
| 5,866,626 | A | * 2/1999 | Blampied et al. |
| 6,306,919 | B1 | * 10/2001 | Blampied et al. |

FOREIGN PATENT DOCUMENTS

| | | |
|---|---|---|
| FR | 2595092 | 4/1987 |
| FR | 2595093 | 4/1987 |
| GB | 1115145 | 5/1968 |
| GB | 1264255 | 2/1972 |
| GB | 1302481 | 10/1973 |
| GB | 2271575 | 4/1994 |
| GB | 2273107 | 6/1994 |
| WO | 99/16816 | 4/1999 |

OTHER PUBLICATIONS

Mark, Herman F., *Cyclopentadiene and Dicyclopentadiene* Kirk–Othmer Encyclopedia of Chemical Technology, 3$^{rd}$ Edition, vol. 7 (1984), pp. 417–429.

Gasanov, A.G., et al., *Catalytic Monomerization of Dicyclopentadiene on γaluminum Oxide in a Continuous–flow System*, Neftekhimiya (1990), 30(1), 69–72 (Abstract).

Brian D. Joyner, et al., *Hydrocarbons Study Report*, OORG Production Working Group, Appendix I, pp. 4–30, Apr. 1995.

* cited by examiner

*Primary Examiner*—Morton Foelak
(74) *Attorney, Agent, or Firm*—Andrew B. Griffs; Louis N. Moreno

(57) ABSTRACT

A thermosetting plastic foam solid formed from the reaction product of: (a) either polyisocyanate or isocyanate-based foam; (b) a polyol-based foam; (c) a catalyst which is capable of promoting the thermosetting reaction between the polyisocyanate or isocyanate-based foam and the polyol-based foam; and (d) a blowing agent which comprises a high purity cyclopentane product, wherein the high purity cyclopentane product is about 95% or greater pure cyclopentane, and, optionally, (e) water and/or (f) liquid flame retardant.

8 Claims, 1 Drawing Sheet

METHOD OF PRODUCING RIGID FOAMS AND PRODUCTS PRODUCED THEREFROM

This application is a continuation under Rule 1.53(b) of U.S. patent application Ser. No. 09/425,813, filed Oct. 25, 1999, which is a continuation-in-part application of U.S. patent application Ser. No. 08/498,276, filed on Jul. 3, 1995, now U.S. Pat. No. 5,578,652 and U.S. Provisional Patent Application No. 60/024031, filed on Aug. 6, 1996, which are incorporated herein by reference.

This invention pertains to methods of producing thermosetting plastic foams utilizing any suitable catalyst to create exothermic heat, which heat in turn causes the unique expansion agent of this invention to vaporize, thereby creating small cells and a low density thermoplastic foam, as well as foams produced by such methods. Examples of such foams include polyurethane foams, polyurethane modified polyisocyanurate foams, and condensation reaction foams such as the formaldehyde series of urea, melamine, and phenol used for thermal insulation.

BACKGROUND

Cellular organic rigid thermosetting plastic foams used for thermal insulation are well known in the art. Foams can be made with urethane linkages, or made with a combination of both isocyanurate linkages and urethane linkages, or they can be made via the well known condensation reactions of formaldehyde with phenol, urea, and melamine. All such plastic foams must utilize an expansion agent, often referred to as a "blowing agent".

The prior art is replete with references to techniques of expanding foam cells. For many years, the dominant blowing agent for all thermosetting foams was trichloromonofluoromethane (CFC-11). Other types of blowing agents have been proposed, such as the use of hydrocarbon mixtures, taught in U.S. Pat. No. 3,558,531. In recent years, various foam expansion methods have been taught in such United States patents as the following (all of which are incorporated herein by reference): U.S. Pat. Nos. 3,993,609, 4,636,529, 4,898,893, 4,927,863, 4,981,876, 4,981,880, 4,986,930, 4,996,242, 5,032,623, 5,070,113, 5,096,933, 5,114,986, 5,130,345, 5,166,182 5,182,309, 5,205,956, 5,213,707, 5,227,088, 5,234,967, 5,236,611, 5,248,433, 5,262,077, 5,277,834, 5,278,196, 5,283,003, 5,290,823, 5,296,516, 5,304,320, 5,314,926, 5,318,996, and 5,336,696.

The relatively recent hydrogenated chlorofluorocarbons (called "HCFCs") are considered to be environmentally friendly expansion agents, but still contain some chlorine, and therefore have an "Ozone Depletion Potential" (called "ODP"). Because of the ODP, the HCFCs have been mandated for eventual phaseout.

Another known class of blowing agents is the non-chlorinated, partially hydrogenated fluorocarbons (called "HFCs") which have the general formula: $H_xF_yC_z$, where x, y, and z are integers. The HFC compounds being proposed for future blowing agents have two serious defects: (1) high intrinsic thermal conductivity properties (i.e., poor thermal insulation); and, (2) expense. In view of the fact that approximately ten percent by weight of rigid foam insulation are the compounds used as blowing agents, high cost combined with the poor insulating value render HFCs less attractive candidates for blowing agents in commercial foam insulation.

Hydrocarbon blowing agents are also known, which class includes halogen-free and $CO_2$-free blowing agents. For example, U.S. Pat. No. 5,182,309 to Hutzen teaches the use of iso- and normal-pentane in various emulsion mixtures. Another example of hydrocarbon blowing agents is taught by Volkert in U.S. Pat. No. 5,096,933, pointing out the virtues of commercial cyclopentane distilled and extracted from natural gas wells.

However, the hydrocarbon blowing agents mentioned in connection with such prior art have inadequate miscibility with polyester polyols, commonly used in polyisocyanurate modified polyurethane foam. The use of these alkanes require a chemical surfactant to obtain a suitable mixture. An improvement in the problem of poor miscibility is taught in U.S. Pat. No. 5,166,182 to Blanpied, whereby the use of azeotropes with polar organic solvents enhance the miscibility with polar polyester polyols. However, all of that work was done using cyclopentane extracted from natural gas.

Another problem with some of these alkanes is the poor insulating value. For example, the thermal conductivity of n-butane at 25° C. is 16.3 mW/m*°K, and n-pentane at 25° C. is 14.8 mW/m*°K.

None of the prior art patents known to Applicants discuss how the cyclopentane is obtained for the disclosed foaming process, nor is there any recognition that any certain mode of cyclopentane production may endow the cyclopentane with properties which are beneficial for a foaming operation.

Although some cyclopentane originates from petroleum, most cyclopentane originates from natural gas wells, and is extracted as the bottom layer of distillation in a refinery, allowing the lighter molecules to be transferred through the natural gas pipeline network. Cyclopentane obtained by extraction contains impurities. In fact, cyclopentane sold as "Technical Grade" contains from 22% to 30% impurities.

One route for manufacturing cyclopentane involves recovery by distillation from naphtha streams derived from crude oil or field natural gasoline. Very limited quantities of cyclopentane can be produced via this route due to the low concentrations of naturally occurring cyclopentane. Furthermore, cyclopentane product purity via this route is limited to approximately 75% by the presence of 2,2-dimethyl butane (which has a boiling point less than 1° F. (0.55° C.) different from cyclopentane). Further purification requires more expensive processing such as extractive distillation.

Extracted cyclopentane ("EXTRCP") has at least five problems which heretofore virtually prohibited it from being considered a serious candidate as a commercial blowing agent for rigid foam insulation. The first problem is that its limited supply is considerably below the amount needed is to meet the quantity demanded of a commercial compound. The second problem is that this inadequate supply contains at least twenty-two percent impurities in the form of hexane isomers and n-pentane, which impurities significantly reduce insulating value of foam made therefrom. The third problem is that extracted cyclopentane is not miscible with the common polyester polyols which are used with HCFCs nor those that were used with CFC-11.

The fourth problem is that extracted cyclopentane does not reduce the viscosity of the polyester polyol foamable blend to a workable level, even when liquid fire retardants are utilized.

The fifth problem is that the foam produced with EXTRCP will not pass the ASTM E-84 maximum 75 Flame Spread Index even with moderate flame retardant.

With respect to the third and fourth above-mentioned problems, the above-discussed U.S. Pat. No. 5,096,933 to Volkert, while generally alluding to the use of polyester polyols, provides no specific example using polyester polyols. The lack of any specific example is consistent with the present inventors' understanding that mixtures made from polyester polyols and extracted cyclopentane are unstable mixtures. In this regard, extracted cyclopentane is no more suitable as a miscible blowing agent than n-pentane or iso-pentane. All three require chemical surfactants for miscibility.

Perhaps the largest obstacle to the use of hydrocarbon blowing agents in the United States is the fifth problem—flammability of thermoset plastics blown with hydrocarbon blowing agents. U.S. Pat. No. 5,096,933 to Volkert mentions disadvantages caused by the flammability of the cycloalkanes. Volkert alludes to the optional use of flame retardants, but provides no example utilizing a flame retardant. Furthermore, none of the five Polyurethane Rigid Foam examples shown by Volkert would pass the maximum Flame Spread Index (FSI) of 75 (ASTM E-84) required of construction foam in the United States. Likewise, a polyisocyanurate foam, without flame retardant, having an Isocyanate-to-Polyester Polyol INDEX of 2.3 badly failed the ASTM E-84 maximum Flame Spread Index requirement of 75, by achieving a 2174 FSI.

With regard to flammability, it is well known that organic surfactants contribute to the flammability of rigid plastic foam insulation. The three main classes of organic surfactants (anionic, cationic, and nonionic) all add to the flammability problem of plastic foam. However, the use of organic carbonates, such as ethylene carbonate and propylene carbonate, does not increase the flammability of plastic foam.

TABLE I describes experiments attesting to the immiscibility of extracted cyclopentane with the polyester polyol having the most miscible potential with non-polar hydrocarbons, as well as the immiscibility of n-pentane and iso-pentane with this polyester polyol. The first column of TABLE I shows the weight ratio of polyester polyol to hydrocarbon blowing agent, with the proposed blowing agents n-pentane, iso-pentane, and extracted cyclopentane being shown in the second through fourth columns, respectively. In all experiments, the polyester polyol utilized was Stepanpol PS-2502A, which (along with Cape's 245-C) is known to have the best miscibility with non-polar hydrocarbon blowing agents. In the experiments reflected by the first row of TABLE I, pure (no other chemicals) PS-2502A polyol was used at 80% weight with 20% by weight pentane; and so forth as indicated in the first column of TABLE I. Significantly, all experiments showed the polyester polyol to be immiscible with extracted cyclopentane, just as it is with n-pentane and iso-pentane.

TABLE I

IMMISCIBILITY STUDIES

| Weight Ratio (Polyol/Blowing Agent) | N-Pentane | Iso-Pentane | Extracted Cyclopentane |
|---|---|---|---|
| 80/20 | Separates | Separates | Separates |
| 75/25 | Separates | Separates | Separates |
| 70/30 | Separates | Separates | Separates |
| 50/50 | Separates | Separates | Separates |
| 35/65 | Separates | Separates | Separates |
| 20/80 | Separates | Separates | Separates |

The fourth problem of extracted cyclopentane (EXTRCP) is shown in TABLE II below, where viscosity is high when blended in foamable blends.

TABLE II

| CHEMICALS: | Pbw | Pbw | Pbw | Pbw | Pbw | Pbw | Pbw | Pbw | Pbw | Pbw |
|---|---|---|---|---|---|---|---|---|---|---|
| PS-2502A | 100 | 100 | 100 | 100 | 100 | 100 | 100 | 100 | 100 | 100 |
| Fyrol PCF | — | — | — | — | — | 15 | 15 | 15 | 15 | 15 |
| Dabco K-15 | 4.0 | 4.0 | 4.0 | 4.0 | 4.0 | 4.0 | 4.0 | 4.0 | 4.0 | 4.0 |
| PM-DETA | 0.2 | 0.2 | 0.2 | 0.2 | 0.2 | 0.2 | 0.2 | 0.2 | 0.2 | 0.2 |
| DC-5357 | 2.0 | 2.0 | 2.0 | 2.0 | 2.0 | 2.0 | 2.0 | 2.0 | 2.0 | 2.0 |
| Water | — | — | — | — | — | 1.8 | 1.8 | 1.8 | 1.8 | 1.8 |
| Prop Carb | — | 5.0 | 10 | — | — | — | 5.0 | 10 | — | — |
| Tex NP-9 | — | — | — | 5.0 | 10 | — | — | — | 5.0 | 10 |
| EXTRCP | 20. | 20. | 20. | 20. | 20. | 23. | 23. | 23. | 23. | 23. |
| Brookfield Viscosity | 6928 | 4016 | 2392 | 4480 | 2880 | 2725 | * | * | 1810 | 1124 |

*denotes that an unstable emulsion separated (broke) rapidly.
Viscosity cps at 65° F.

TABLE II shows that, without exception, every blend made with extracted cyclopentane produced a Brookfield-viscosity over 1000 cps at 65° F., even one with 10 parts by weight of a strong viscosity reducer, Texacols NP-95. The foamable blends using both Fyrol PCF and Propylene Carbonate mixed into an unstable emulsion which soon separated. The inability to formulate with both liquid flame retardant and an organic carbonate is a serious obstacle to obtaining both flame resistance and a low enough viscosity to be workable.

In addition to obtaining cyclopentane by extraction, it appears that cyclopentane can also-be synthesized from other hydrocarbons. In this regard, FR-A-2595092 and FR-A-2595093 teach the preparation of catalysts comprised of palladium with another transition metal such as ruthenium or rhodium for the cyclization and hydrogenation of 1,3-pentadiene, as well as the hydrogenation of cyclopentadiene, to cyclopentane. These French Demandes do not teach or suggest the synthesis of cyclopentane from dicyclopentadiene ("DCP"), or make any reference to foaming processes.

GB-A-2271575 and GB-A-2273107 disclose two similar methods for synthesizing cyclopentane from dicyclopentadiene. GB-A-1302481 teaches a method which synthesizes minor amounts of cyclopentane, but preferentially produces cyclopentene. While GB-A-2271575 and GB-A-2273107 mention initially the search for blowing agents for polyurethane foam, neither provides an example of the use of cyclopentane as a blowing agent for foam, much less a foam produced with polyester polyol. In fact, European practice is to make polyurethane foam using polyether polyol rather than polyisocyanurate foam using polyester polyol.

Historically, considerable attention has been directed to the synthesis of cyclopentadiene and various isomers of the pentadiene and pentene building-block monomers. In this regard, dicyclopentadiene ("DCP"), $C_{10}H_{12}$, is the dimer of cyclopentadiene ("CP"), $C_5H_6$, and is the naturally stable form of CP. Cyclopentadiene monomer spontaneously dimerizes at room temperature. DCP is obtained from the thermal cracking of high molecular weight hydrocarbons, such as naphtha and gas oils, particularly in the presence of steam.

Owing to its conjugated double bonds, CP can undergo numerous reactions, and has several important commercial uses. While most commercial CP is obtained from cracking DCP, CP is also obtained from other commercial reactions such as ethylene production. To prevent it from autodimerizing, CP must be cooled to below minus 20° C. To prevent spontaneous oxidation, CP must be protected from atmospheric oxygen. Thus, it is advantageous to convert DCP into cyclopentane in an enclosed reactor utilizing an excess of hydrogen, and adding cyclopentane as a diluent, as shown in GB-A-2271575 and GB-A-2273107.

The thermocatalytic conversion of DCP to CP, and back again, and similar processes, have been well documented. However, such conversion and similar processes have not occurred in the context of utilization for a blowing agent for a rigid insulative foam which utilizes polyester polyol.

The similar processes mentioned above include use by Alder and Stein of palladium as a catalyst to polymerize and hydrogenate DCP into the trimer form, then to tetracyclopentadiene, and finally into pentacyclopentadiene. Hydrogenation and polymerization to tetrahydrotricyclopentadiene has also been accomplished with Adams' platinum catalyst at room temperature and fifty pounds per square inch pressure. Bai, Zhang, and Sachtler of the Center for Catalysis and Surface Science, Northwestern University, reported using palladium adducts in 1991 for cyclization and hydrogenolysis reactions of neopentane and other hydrocarbons. US-A4178455 to Hirai et al. teaches that a transition metal catalyst, with a Lewis acid promoter, will convert urea biurets, and allophanates into corresponding urethanes.

Another possible route for manufacturing cyclopentene involves hydrogenation of cyclopentane; however, cyclopentene is not readily available in commercial quantities.

Another route to produce a high purity cyclopentane, and the subject of the present invention, involves splitting dicyclopentadiene (DCPD) into cyclopentadiene (CPD) monomer and hydrogenating the monomer to form cyclopentane. A key advantage of this route is an abundance of commercially available, low-cost DCPD raw material. Technical obstacles involve: (1) effective splitting of DCPD without forming heavy resins that diminish product yields and foul the splitting equipment; and (2) preventing unwanted reaction of the highly reactive monomer which decreases desired product yield, form unwanted by-products, and can lead to deactivation of the hydrotreating catalyst.

Thus, it is an object of the present invention to provide a thermosetting foam utilizing the advantages of specially synthesized cyclopentane ("SYNCP") as an improved insulating gas inside closed cells.

Another advantage of the present invention is the utilization of a hydrocarbon blowing agent which is readily miscible with common polyester polyols without requiring organic surfactants to make a stable blend.

An advantage of the present invention is the ability to create a foamable blend viscosity low enough to use in existing pumps without the requirement for additional viscosity reducing diluents.

Yet another advantage of the present invention is the utilization of an abundant source of specially synthetically produced cyclopentane, which insures that the costs will be contained in a reasonable range.

Still another advantage of the present invention is the achievement of a thermosetting foam having an ASTM E-84 Flame Spread Index less than the maximum 75 allowed.

SUMMARY OF THE INVENTION

A thermosetting plastic foam solid is obtained using a blowing agent comprised at least partially of the reaction product of the cracking of dicyclopentadiene into essentially pure cyclopentane. This unique cyclopentane hydrocarbon is miscible in polyester polyols, where others, such as extracted cyclopentane, are not. In a blend of 15 parts of liquid flame retardant per hundred parts polyester polyol, the mixture is both stable and has a suitably low viscosity.

The present invention provides a unique method of producing a rigid thermosetting plastic foam which comprises the steps of: blending the following components: either polyisocyanate or isocyanate; a polyol a catalyst which is capable of promoting the thermosetting reaction between the polyisocyanate or isocyanate and the polyol; and a blowing agent comprised at least partially from a high purity cyclopentane product, wherein the high purity cyclopentane product is about 95% or greater pure cyclopentane.

The unique high purity cyclopentane blowing agent according to the present invention is formed by the following steps: (a) cracking dicyclopentadiene to cyclopentadiene; (b) separating the cyclopentadiene-rich stream from the higher boiling liquids; (c) diluting the cyclopentadiene-rich stream with recycled saturates such that cyclopentadiene content is limited to 15–50%; (d) conducting a first hydrogenation of the cyclopentadiene-rich stream in the presence of hydrogen and a palladium-on alumina catalyst, thereby converting a substantial portion of the cyclopentadiene to cyclopentane; (e) conducting a second hydrogenation of the cyclopentane-rich stream from step (d) in the presence of a massive nickel catalyst wherein any residual olefins are saturated to form a crude cyclopentane product; (f) separating hydrogen from the crude cyclopentane product; (g) recycling the hydrogen from step (f) to step (a); and (h) flash stripping the crude cyclopentane product to form a substantially pure cyclopentane product (approximately 95% cyclopentane).

Furthermore, the present invention also pertains to a thermosetting plastic foam solid formed from the reaction product of: (a) either polyisocyanate or isocyanate; (b) a polyol; (c) a catalyst which is capable of promoting the thermosetting reaction between polyisocyanate or isocyanate and the polyol; and (d) a blowing agent which comprises a high purity cyclopentane product, wherein the high purity cyclopentane product is about 95% or greater pure cyclopentane, and, optionally, (e) water and/or (f) liquid flame retardant.

The rigid thermosetting plastic foam preferable exhibits the following properties: an aged R value in the range between about 4–15, more preferably between about 6–8, based on one inch of said rigid thermosetting plastic foam, enhanced structural strength in terms of dimensional stability and compressibility versus conventional thermosetting plastic foams, slow blowing agent diffusion rate, and flame resistance.

This process according to the present invention can also be used to manufacture methylcyclopentane from dimethyldicyclopentadiene.

Other and further objects, advantages and features of the present invention will be understood by reference to the following specification in conjunction with the annexed drawings, wherein like parts have been given like numbers.

DETAILED DESCRIPTION OF THE INVENTION

Figure 1:
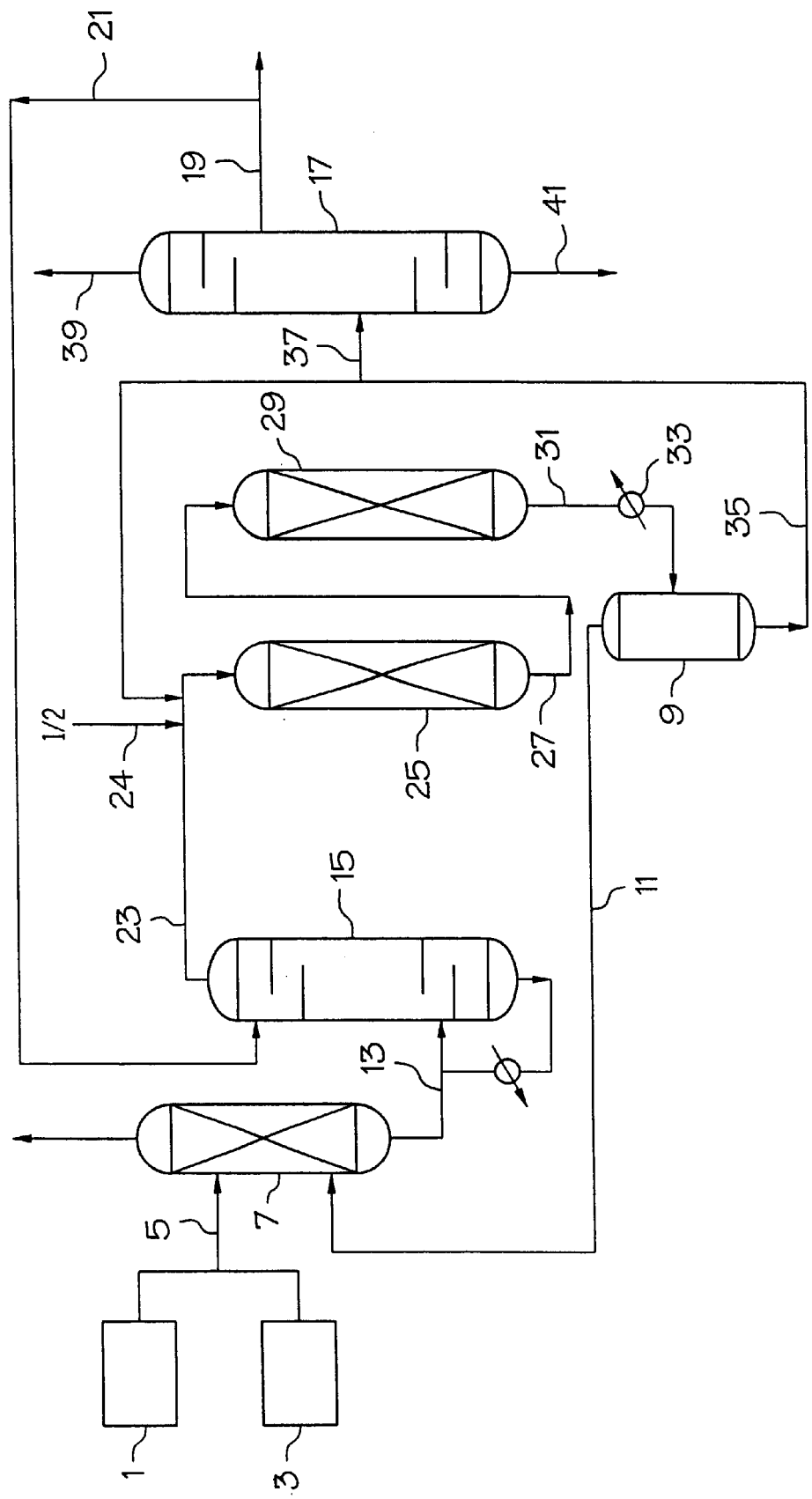
FIG. 1 is a schematic diagram of the cyclopentane process according to the present invention.

It has been surprising to discover that cyclopentane synthesized from dicyclopentadiene ("DCP"), $C_{10}H_{12}$, is miscible with polyester polyols, not requiring additional surfactants or emulsifiers to mix well. As one skilled in the art will now appreciate upon comprehending this discovery, the miscibility of this unique cyclopentane creates a foamable blend having a viscosity low enough to utilize, whereas the EXTRCP does not create this advantage.

The unique, or special, synthesized cyclopentane (SYNCP) utilized in all embodiments of this invention is obtained from Exxon Chemical Americas as imported "Exxsol™ Cyclopentane". In this regard, the cyclopentane utilized in embodiments of this invention is synthetically created by the depolymerization of DCP to CP. The synthetic cyclopentane used in the examples of this invention is in excess of 95% pure cyclopentane.

The simplified equation for synthesized cyclopentane (SYNCP) according to the present invention is as shown as EQUATION 1:

$$C_{10}H_{12} \xrightarrow{\text{depolymerize}} 2C_5H_6 \xrightarrow{\text{catalyst} + 4H_2} 2C_5H_{10}$$

Examples of processes suitable for production of the synthesized cyclopentane (SYNCP) according to the present invention are described in GB-A-2271575 and GB-A-2273107, both of which are incorporated herein by reference. In GB-A-2271575, cyclopentane is used as a diluent, or carrier, during the depolymerization, e.g., "cracking", stage to reduce coking and the formation of trimers, tetramers, and higher polymers which are not readily decomposed to the monomer, as taught in GB-A-1302481, also incorporated herein by reference. In GB-A-2273107, catalyst powder is circulated through reaction zones in a slurry form until it is removed by filtration.

This processing method allows the hydrogenation of the unsaturated monomer to cyclopentane at temperatures below 175° C. The advantages of this process are outlined in GB-A-1115145 and GB-A-1264255, both of which are incorporated herein by reference.

As another example of an implementation of EQUATION 1, the $C_5H_6$ represents the unsaturated five-carbon hydrocarbons, either linear or cyclic. Some pentadiene ($C_5H_8$) may also be present during the conversion. In such process, the cyclopentadiene is hydrogenated to cyclopentane, and the pentadiene may undergo hydrogenation and cyclization to cyclopentane using a catalyst, e.g., a transition metal (or adducts thereof) catalyst. An example of a palladium metal adduct is $PdCl_2$.

A process for manufacturing high-purity (i.e., 95% or greater) cyclopentane by splitting dicyclopentadiene and completely hydrogenating the cyclopentadiene monomer in a single unit as illustrated in attached FIG. 1.

The general process scheme involves diluting commercially available dicyclopentadiene with an aliphatic hydrocarbon fluid of specific volatility and solvency. This material is then introduced into a distillation apparatus in which the dicyclopentadiene decomposes (or depolymerizes) to cyclopentadiene monomers. Reflux to the distillation apparatus consists of a cyclopentane product recycle stream. This reflux aids distillation and dilutes the cyclopentadiene monomer to prevent re-dimerization and cyclopentadiene yield reduction. The overhead stream from this step is a stream containing cyclopentane and cyclopentadiene.

This stream is further diluted with cyclopentane-rich recycle liquid obtained from the high-pressure separator drum. The purpose of the dilution is to minimize cyclopentadiene dimerization and to allow controlling of the exotherm in the subsequent hydrotreating reactors.

The cyclopentadiene/cyclopentane stream is then pumped to a reactor and combined with a stoichiometric excess of hydrogen contained in a treatgas stream. It is then passed over a palladium-on-alumina catalyst where the bulk of the hydrogenation reaction occurs converting most of the cyclopentadiene to cyclopentane. The first reactor effluent flows to a second reactor containing a massive nickel catalyst where any remaining olefins (i.e., cyclopentene) are saturated.

The fully hydrogenated nickel reactor effluent is cooled and enters a high-pressure flash drum. The vapor from this drum, which contains primarily hydrogen but also contains some cyclopentane vapor, is contacted with the dicyclopentadiene feed stream in an absorber tower to minimize cyclopentane losses.

A portion of the liquid product from the high-pressure separator drum is recycled as described earlier. The remainder flows to a product stripping tower in which any remaining dissolved hydrogen and any compounds heavier than cyclopentane are removed. The stripper bottoms may be recycled to the dicyclopentadiene cracking tower.

The process according to the present invention can best be described by referring to FIG. 1, wherein DCPD and an aliphatic hydrocarbon fluid of specific volatility and solvency are fed from tanks 1 and 3, respectively, via conduit 5 to distillation cracking tower 7 such that DCPD is cracked to form cyclopentadiene and cyclopentane. A cyclopentane product recycle stream from a high-pressure flash drum 9 is recycled to tower 7 via conduit 11. The cyclopentane product recycle stream aids distillation in tower 7 and dilutes the cyclopentadiene monomer to between 15–50% to prevent re-dimerization and cyclopentadiene yield reduction. The liquid cyclopentadiene and cyclopentane mixture is taken as bottoms from tower 7 via conduit 13, and delivered to separator drum 15 where it is further diluted with cyclopentane-rich recycle liquid obtained from product stripping tower 17 via conduits 19 and 21. The purpose of the dilution in separator drum 15 is to minimize cyclopentadiene dimerization and to allow controlling of the exotherm in the subsequent hydrotreating reactors. The cyclopentadiene/cyclopentane stream having a cyclopentadiene content of between about 15–50% is taken overhead from separator drum 15 via conduit 23 and mixed with a stoichiometric excess of hydrogen from conduit 24. The hydrogen saturated cyclopentadiene/cyclopentane stream is then sent to first hydrogenation reactor 25 wherein it is passed over a palladium-on-alumina catalyst where the bulk of the hydrogenation reaction occurs converting most of the cyclopentadiene to cyclopentane. The liquid effluent from first hydrogenation reactor 25 is taken via conduit 27 and sent to the top of second hydrogenation reactor 29 containing a massive nickel catalyst where any remaining olefins (i.e., cyclopentene) are saturated.

The fully hydrogenated product stream is taken as liquid bottoms from reactor 29 via conduit 31 and cooled via heat exchanger 33 and thereafter sent to high-pressure flash drum 9. The overhead (i.e., primarily hydrogen, but also containing some cyclopentane vapor) from flash drum 9 is returned to tower 7 via conduit 11, as discussed before, to minimize cyclopentane losses. The bottoms from flash drum 9 are taken via conduit 35 and either recycled upstream of first hydrogenation reactor 25 or sent via conduit 37 to product stripping tower 17 wherein any remaining dissolved hydrogen and any compounds heavier than cyclopentane are removed overhead via conduit 39. The bottoms from stripping tower 17 are removed via conduit 41 and, optionally, recycled to tower 7 or purged from the system. Cyclopentane product is recovered from an intermediate section of stripper tower 17 via conduit 19 and either sent to tankage, not shown, or recycled via conduit 21 to separator drum 15, as discussed above. The cyclopentane is preferably 95% pure cyclopentane at this point.

The unique cyclopentane product produced in accordance with the present invention is particularly useful in a method of producing a rigid thermosetting plastic foam described in co-pending and commonly assigned U.S. Ser. No. 08/389,955, filed Feb. 17, 1995, and U.S. Ser. No. 08/498,276, filed Jul. 3, 1995 (now U.S. Pat. No. 5,578,652), which are incorporated herein by reference. The method of producing a rigid thermosetting plastic foam comprises the steps of: blending the following components: either polyisocyanate or isocyanate; a polyol; a catalyst which is capable of promoting the thermosetting reaction between the polymeric polymethylene polyphenylisocyanate and the polyol; and a blowing agent which comprises a high purity cyclopentane product, wherein the high purity cyclopentane product is about 95% or greater pure cyclopentane.

Some of the key advantages of high purity cyclopentane product, such as Exxsol® Cyclopentane over conventional blowing agents such as low purity cyclopentanes, pentane isomers and hydrofluorocarbons are: (1) the high purity cyclopentane product of the present invention is soluble or miscible in polyols, whereas n-pentane and isopentane are not soluble in polyols; (2) insulating efficiency of thermosetting plastic foams formed using high purity cyclopentane product of the present invention is higher than with other pentane isomers for initial and aged R values; (3) high purity cyclopentane products of the present invention have a much slower diffusion rate out of polyurethane foams than other pentane isomers; and (4) high purity cyclopentane product have no GWP, whereas hydrofluorocarbon blowing agents have a high GWP.

The following is a comparison of various blowing agents' properties:

| Blowing Agents | HCFC 141b* | HFC 245FA** | HFC 365*** | 95% CP | 78% CP | Iso-Pen. | N-Pen. |
|---|---|---|---|---|---|---|---|
| Molecular Wt. | 117 | 134 | 148 | 70 | 70 | 72 | 72 |
| Vapor Thermal Conductivity BTU-in/hr-ft², 25° C. | 0.005 | 0.007 | 0.008 | 0.0065 | 0.0068 | 0.0076 | 0.0076 |
| Soluble in Polyols | Yes | Yes | Yes | Yes | No | No | No |
| Boiling Point, ° C. | 32.1 | 15.4 | 40 | 50 | 50 | 28 | 28 |
| Flammability | Slight | None | Yes | Yes | Yes | Yes | Yes |
| Ozone Depletion | 0.12 | 0 | 0 | 0 | 0 | 0 | 0 |
| Global Warming | 0.12 | 0.24 | >0.20 | None | None | None | None |
| VOC Status | No | No | No | Yes | Yes | Yes | Yes |

*$CH_3CCl_2F$
**$CF_3CH_2CHF_2$ manufactured by Allied Signal Inc.
***$CF_3CH_2CF_2CH_3$ manufactured by Elf Atochem.
CP denotes cyclopentane having the general formula $C_5H_{10}$.
Iso-Pen. denotes iso pentane having the general formula $C_5H_{12}$.
N-Pen. denotes normal pentane having the general formula $C_5H_{12}$.

The miscibility of the specially synthesized cyclopentane (SYNCP) of the invention is evidenced by TABLE III.

Furthermore, the addition of a potassium catalyst, a tertiary amine catalyst, and the normal silicone type surfactant to the above blends of synthesized cyclopentane (SYNCP) produces clear solutions in the useful ranges of from about 13% up to about 30% cyclopentane by weight. By contrast these same additives do not make clear solutions of any ratio blend with the three blowing agents of TABLE I.

TABLE III (MISCIBILITY STUDIES OF THE PRESENT CYCLOPENTANE)

| Weight Ratio of Polyol/Cyclopentane | Synthesized Cyclopentane |
|---|---|
| 80/20 | Stable Mixture |
| 75/25 | Stable Mixture |
| 70/30 | Stable Mixture |
| 50/50 | Stable Mixture |
| 35/65 | Stable Mixture |
| 20/80 | Stable Mixture |

In contrast to the high viscosities shown in TABLE II utilizing extracted cyclopentane, as shown in TABLE IV foamable mixtures using the specially synthesized cyclopentane (SYNCP) of the invention have low viscosities. Furthermore, the mixtures of the invention were all clear solutions and remained stable.

It is well known that organic surfactants contribute to plastic foam flammability, whereas propylene carbonate does not. Thus, the foam of Example 8 in TABLE IV utilizing 10 pphp propylene carbonate has a lower Flame Spread Index than the foam of Example 10 utilizing 10 pphp ethoxylated nonylphenol (Texaco NP-95). Advantageously, Example 8 also has a lower viscosity than Example 10, although both are low enough to use easily. Thus, the use of an organic carbonate in place of an organic surfactant is a major advantage not available to the extracted cyclopentane (EXTRCP), as evidenced by the broken emulsions in TABLE II.

Thus it can be seen by comparing TABLE II with TABLE IV, that the synthesized cyclopentane affords lower, workable viscosities even at the low temperature of 65° F.

Table V shows blends with, and without, liquid flame retardants (Fyrol PCF), with either extracted cyclopentane (EXTRCP) or synthetic cyclopentane (SYNCP), as well as their Brookfield viscosities at 77° F.

TABLE VI (VAPOR THERMAL CONDUCTIVITY)

| BLOWING AGENT | mW/m ° K. at 25° C. | BTU in/hr*ft$^{2}$* ° F. at 140° F. |
|---|---|---|
| CFC-11 | 7.80 | 0.0648 |
| HCFC-141b | 9.80 | 0.0960 |
| n-Pentane | 4.80 | 0.1080 |
| SYNCP | 12.10 | 0.0864 |

TABLE IV (Foamable Blend Examples 1–10)

| CHEMICALS: | Ex 1 Pbw | Ex 2 Pbw | Ex 3 Pbw | Ex 4 Pbw | Ex 5 Pbw | Ex 6 Pbw | Ex 7 Pbw | Ex 8 Pbw | Ex 9 Pbw | Ex 10 Pbw |
|---|---|---|---|---|---|---|---|---|---|---|
| PS-2502A | 100 | 100 | 100 | 100 | 100 | 100 | 100 | 100 | 100 | 100 |
| Fyrol PCF | — | — | — | — | — | 15 | 15 | 15 | 15 | 15 |
| Dabco K-15 | 4.0 | 4.0 | 4.0 | 4.0 | 4.0 | 4.0 | 4.0 | 4.0 | 4.0 | 4.0 |
| PM-DETA | 0.2 | 0.2 | 0.2 | 0.2 | 0.2 | 0.2 | 0.2 | 0.2 | 0.2 | 0.2 |
| DC-5357 | 2.0 | 2.0 | 2.0 | 2.0 | 2.0 | 2.0 | 2.0 | 2.0 | 2.0 | 2.0 |
| Water | — | — | — | — | — | 1.8 | 1.8 | 1.8 | 1.8 | 1.8 |
| Prop Carb | — | 5.0 | 10 | — | — | — | 5.0 | 10 | — | — |
| Tex NP-95 | — | — | — | 5.0 | 10 | — | — | — | 5.0 | 10 |
| SYNCP | 20. | 20. | 20. | 20. | 20. | 23. | 23. | 23. | 23. | 23. |
| Brookfield Vis. cPs at 65° F. | 3416 | 2680 | 1248 | 3104 | 2200 | 2148 | 1344 | 874 | 1432 | 942 |

TABLE V (Foamable Blend Examples 11–22)

| CHEMICALS: | Ex 11 Pbw | Ex 12 Pbw | Ex 13 Pbw | Ex 14 Pbw | Ex 15 Pbw | Ex 16 Pbw | Ex 17 Pbw | Ex 18 Pbw | Ex 19 Pbw | Ex 20 Pbw | Ex 21 Pbw | Ex 22 Pbw |
|---|---|---|---|---|---|---|---|---|---|---|---|---|
| PS-2502A | 100 | 100 | 100 | 100 | 100 | 100 | 100 | 100 | 100 | 100 | 100 | 100 |
| Fyrol PCF | — | — | — | — | — | 15 | 15 | 15 | 15 | 15 | 15 | 15 |
| Dabco K-15 | 4.0 | 4.0 | 4.0 | 4.0 | 4.0 | 4.0 | 4.0 | 4.0 | 4.0 | 4.0 | 4.0 | 4.0 |
| PM-DETA | 0.2 | 0.2 | 0.2 | 0.2 | 0.2 | 0.2 | 0.2 | 0.2 | 0.2 | 0.2 | 0.2 | 0.2 |
| Silicon | 2.6 | 2.6 | 2.6 | 2.6 | 2.6 | 2.6 | 2.6 | 2.6 | 2.6 | 2.6 | 2.6 | 2.6 |
| EXTRCP | 21.7 | — | 25.3 | — | 29.1 | — | 21.7 | — | 25.3 | — | 29.1 | — |
| SYNCP | — | 21.7 | — | 25.3 | — | 29.1 | — | 21.7 | — | 25.3 | — | 29.1 |
| Brookfield Vis. cPs at 77° F. | 5320 | 3168 | 6072 | 3120 | 7192 | 3160 | 2120 | 1408 | 2336 | 1440 | 3552 | 1680 |

One skilled in the art will notice a unique situation: with both versions of cyclopentane, as the amount of cyclopentane increases, so does the viscosity. This is in contrast to prior art blowing agents, which decrease viscosity with increased amount of blowing agent. Nevertheless, it is evident from TABLE V data that synthesized cyclopentane (SYNCP) not only produces lower viscosities than extracted cyclopentane (EXTRCP), the viscosities produced with about 15 parts by weight (per hundred polyol) liquid flame retardant added are low enough (below 1700 cps) to be easily used in any foam machinery. Conversely, without a liquid flame retardant being utilized, the viscosities are over 3000 cps.

Vapor thermal conductivity properties of four blowing agents are shown below in TABLE VI, including one blowing agent from the past (CFC-11), one blowing agent from the present (HCFC-141b), a purported blowing agent of the future (n-Pentane), and the SYNCP blowing agent of the present invention.

It should be noted that at higher temperatures (140° F.), the SYNCP exhibits a better intrinsic insulation value than the currently utilized HCFC-141b. In general, TABLE VI shows the advantage of SYNCP over n-pentane as a potential future insulating gas.

TABLE VII shows thermosetting. foam examples and illustrates the surprising differences between extracted (EXTRCP) and synthesized cyclopentane (SYNCP) of the present invention. Thus, TABLE VII demonstrates that when the extracted cyclopentane (EXTRCP) is compared directly to synthesized cyclopentane (SYNCP), the synthesized cyclopentane of the present invention shows unexpected and favorable results. All examples of the synthesized cyclopentane show better k-factors, and lower densities. All of the friabilities were lower than foam blown with prior art blowing agents. At the higher 3.0 Index, and the highest water level (0.85 parts per hundred parts polyol), the synthesized cyclopentane produced a foam with 24.5% lower friability than the extracted cyclopentane counterpart.

TABLE VII (THERMOSETTING FOAM EXAMPLES 1–8)

| COMPONENT (Pbw) | Ex. 1 | Ex. 2 | Ex. 3 | Ex. 4 | Ex. 5 | Ex. 6 | Ex. 7 | Ex. a |
|---|---|---|---|---|---|---|---|---|
| PS-2502A | 100.0 | 100.0 | 100.0 | 100.0 | 100.0 | 100.0 | 100.0 | 100.0 |
| Potassium Cat. | 2.7 | 2.7 | 3.0 | 3.0 | 3.2 | 3.2 | 4.0 | 4.0 |
| Tertiary Amine | 0.2 | 0.2 | 0.2 | 0.2 | 0.15 | 0.15 | 0.15 | 0.15 |
| Silicone | 2.2 | 2.2 | 2.1 | 2.1 | 2.1 | 2.1 | 2.0 | 2.0 |
| Water | — | — | — | — | 0.68 | 0.68 | 0.85 | 0.85 |
| EXTRCP | — | 24.0 | — | 26.9 | — | 23.4 | — | 26.7 |
| SYNCP | 24.0 | — | 26.9 | — | 23.4 | — | 26.7 | — |
| TOTAL B-SIDE | 129.1 | 129.1 | 132.2 | 132.2 | 129.53 | 129.53 | 133.7 | 133.7 |
| Lupr. M70L | 146.7 | 146.7 | 176.7 | 176.7 | 170.3 | 170.3 | 208.9 | 208.9 |
| Silicone | 0.4 | 0.4 | 0.5 | 0.5 | 0.4 | 0.4 | 0.5 | 0.5 |
| TOTAL A-SIDE | 147.1 | 147.1 | 177.2 | 177.2 | 170.7 | 170.7 | 209.4 | 209.4 |
| TOTAL FOAM | 276.2 | 276.2 | 309.4 | 309.4 | 300.23 | 300.23 | 343.1 | 343.1 |
| INDEX, NCO/OH | 2.5 | 2.5 | 3.0 | 3.0 | 2.5 | 2.5 | 3.0 | 3.0 |
| DENSITY, PCF | 1.6 | 1.7 | 1.6 | 1.7 | 1.5 | 1.6 | 1.6 | 1.7 |
| CREAM TIME | 15" | 19" | 19" | 20" | 22" | 23" | 21" | 22" |
| GEL TIME | 30" | 30" | 28" | 29" | 39" | 42" | 42" | 43" |
| STRING TIME | 44" | 44" | 43" | 43" | 48" | 49" | 51" | 52" |
| TACK FREE | 47" | 46" | 45" | 46" | 52" | 53" | 53" | 55" |
| FRIABILITY, % Weight Lose | 2.57 | 2.39 | 2.94 | 2.61 | 3.60 | 2.96 | 7.88 | 10.43 |
| INITIAL k | 0.1401 | 0.1539 | 0.1397 | 0.1528 | 0.1377 | 0.1515 | 0.1397 | 0.1508 |
| Percent Better R-Value with SYNCP | 9.9% | | 9.4% | | 10.0% | | 8.0%; | |

To further put the potential future insulating gases in perspective, several proposed HFC gases are shown in TABLE VIII with the pentane isomers and the prior art fluorocarbons, showing respective insulation data.

TABLE VIII

| | VAPOR THERMAL CONDUCTIVITY: | | | |
|---|---|---|---|---|
| BLOWING | BTU in/hr*ft$^2$ ° F. | | mW/m ° K. | |
| AGENT | [1]at 140° F. | [2]at 44° C. | [3]at 20° C. | [4]at 25° C. |
| CFC-11 | 0.0648 | 0.064 | 8.4 | 7.8 |
| HCFC-141b | 0.0960 | 0.084 | 9.7 | 9.8 |
| HFC-245ca | — | 0.092 | 13.3 | — |
| HFC-245fa | — | — | — | — |
| HFC-356mffm | — | 0.102 | — | — |
| HFC-365mfc | — | — | 10.6 | — |
| SYNCP | 0.0864 | — | 12.0 | 12.1 |
| n-pentane | 0.1080 | — | — | 14.8 |

[1]Dow Chemical Company.
[2]Knopeck, Parker, Richard, Shankland, "Polyurethanes, 1994, Page 116.
[3]Murphy, J., & Costa, J., 'Polyurethanes 1994', Proceedings, Page 323.
[4]BASF Chemical Company.
(Different data sources show slightly different conductivity values.)

By noting the lambda values in the third column of TABLE VIII, one can compare cyclopentane (SYNCP) to HFC-245ca and HFC-365mfc. Then, by using HFC-245ca to interpolate that data into the second column, one can see that SYNCP has a better intrinsic insulating value than three of the four HFCs listed.

In view of the foregoing, preferably the foamable blend which contains most of the synthesized cyclopentane also utilizes a liquid fire retardant. The most preferred embodiments of the instant invention also utilize (1) a lower boiling point alkane blowing agent with the specially synthesized cyclopentane (SYNCP) to increase internal cell gas pressure as a protection against shrinkage and [optionally] (2) a polar organic blowing (e.g, expansion) agent which azeotropes with cyclopentane such as taught in U.S. Pat. No. 5,166,182, or a viscosity depressant such as propylene carbonate or the non-ionic surfactants such as ethoxylated nonylphenol. The latter are especially useful if the foamable blend is to be cooled below 70° F. prior to use.

Suitable flame retardants utilized in the invention include, but are not limited to, tri(2-chloroisopropyl)phosphate, tricresyl phosphate, tri(2-chloroethyl)phosphate, tri(2,2-dichloroisopropyl)phosphate, diethyl N,N-bis(2-hydroxyethyl) aminomethylphosphonate, dimethyl methylphosphonate, tri(2,3-dibromopropyl)phosphate, tri(1,3-dichloropropyl)phosphate, and tetra-kis-(2-chloroethyl) ethylene diphosphate.

The isocyanates utilized may be any organic isocyanate. However, the most preferred type is the polymeric polymethylene polyphenylisocyanate having an average functionality of between 2.0 and 3.5.

The polyester polyols preferred for this invention are those aromatic organic esters based upon one, or a combination, of the phthalate isomers linked together with mixed glycols, predominately diethylene glycol.

Any of the prior art catalysts and cell stabilizing surfactants may be utilized. However, the potassium-organo-salt catalysts are preferred. Thermosetting Foam Examples 9 through 15 in TABLE IX show the most preferred foam formulations.

In thermosetting Foam Examples 9 through 15, any HCFC or HFC may be substituted for, or mixed with, any of the additional expansion agents; e.g., propane, iso-butane, acetone, methyl/ethyl alcohol, or methyl acetate. One skilled in the art will recognize that other combinations of the components shown in TABLE IX can be interchanged, or intermixed, or added at different levels, to provide a thermosetting foam with different properties.

Advantageously, the abundance of DCP makes it an ideal raw material for the synthesis of pure cyclopentane according to the present invention.

As an additional advantage, as understood with reference to the foregoing examples, the use of SYNCP facilitates the use of little or no organic surfactants for either comparability or viscosity reduction, so that the foamable blends of the present invention are substantially devoid of organic surfactants.

Thermosetting Foam Examples 16 and 17 (see TABLE X) show the use of polyether polyols in conjunction with polyester polyols. These foams are suitable for non-construction foams used in the United States, such as appliance insulation, and for a wide range of foreign (e.g., European) rigid foam applications, including building construction. Ranging from an Index of 1.5 up to 3.0, the foams of Examples 16 and 17 provide good insulating properties with differing flammability resistance.

For the present invention, a majority (e.g., greater than 50% parts by weight) of the polyol component should be polyester polyol, although as shown in TABLE X a minority of the polyol component may be a polyether polyol (e.g., Voranol 280).

When selecting various flame retardants, the advantages of synthetic cyclopentane (SYNCP) was again demonstrated. As in TABLE IV and TABLE V above, TABLE XII below shows the Brookfield viscosities of blend examples 23A–23F of TABLE XI. Blend examples 23A–23F differ only in the particular flame retardant utilized (the same amount of flame retardant being utilized in each example). As seen in TABLE XI, the only flame retardant soluble in both types of pentane (e.g., both SYNCP and EXTRCP) is Fyrol PER.

TABLE IX (THERMOSETTING FOAM EXAMPLES 9–15)

| COMPONENT, pbw | Ex. 9 | Ex. 10 | Ex. 11 | Ex. 12 | Ex. 13 | Ex. 14 | Ex. 15 |
|---|---|---|---|---|---|---|---|
| PS-2502A | 100.0 | 100.0 | 100.0 | 100.0 | 100.0 | 100.0 | 100.0 |
| Fyrol PCF | 15.0 | 15.0 | 15.0 | 15.0 | 15.0 | 15.0 | 15.0 |
| Dabco K-15 | 4.0 | 4.0 | 4.0 | 4.0 | 4.0 | 4.0 | 4.0 |
| Amine Cat. | 0.3 | 0.3 | 0.3 | 0.3 | 0.3 | 0.3 | 0.3 |
| Silicone | 2.5 | 2.5 | 2.5 | 2.5 | 2.5 | 2.5 | 2.5 |
| Prop. Carb. | 5.0 | 10.0 | 10.0 | 10.0 | 10.0 | 10.0 | 10.0 |
| Texaco NP95 | 5.0 | 0.0 | 0.0 | 0.0 | 0.0 | 0.0 | 0.0 |
| Acetone** | 0.0 | 0.0 | 0.0 | 10.44 | 0.0 | 0.0 | 0.0 |
| Methyl Acetate** | 0.0 | 0.0 | 0.0 | 0.0 | 0.0 | 10.99 | 0.0 |
| Methyl Alcohol** | 0.0 | 0.0 | 0.0 | 0.0 | 0.0 | 0.0 | 4.06 |
| Propane*** | 0.0 | 1.0 | 0.0 | 0.0 | 0.0 | 0.0 | 0.0 |
| Iso-Butane*** | 0.0 | 0.0 | 4.1 | 0.0 | 0.0 | 0.0 | 0.0 |
| Water | 1.5 | 0.0 | 0.0 | 0.0 | 0.0 | 0.0 | 0.0 |
| SYNCP | 20.0 | 28.7 | 25.6 | 18.56 | 26.82 | 18.01 | 24.94 |
| TOTAL B-SIDE | 153.3 | 161.5 | 161.5 | 160.8 | 160.8 | 160.8 | 160.8 |
| Lupr. M70L | 230.0 | 178.8 | 178.8 | 178.8 | 178.8 | 178.8 | 178.8 |
| Silicone | 0.5 | 0.5 | 0.5 | 0.5 | 0.5 | 0.5 | 0.5 |
| TOTAL A-SIDE | 230.5 | 179.3 | 179.3 | 179.3 | 179.3 | 179.3 | 179.3 |
| TOTAL FOAM | 383.8 | 340.8 | 340.8 | 340.8 | 340.8 | 340.8 | 340.8 |
| Foam Index | 2.68 | 3.0 | 3.0 | 3.0 | 3.0 | 3.0 | 3.0 |
| Flame Spread Index | 36 | less than 75 | less than 75 | less than 75 | less than 75 | less than 75 | less than 75 |

**"These polar organic expansion agents are mixed at the weight percent ratio with the special synthesized cyclopentane which forms an azeotrope boiling at a lower temperature than either component alone.
***These alkanes are mixed with special synthesized cyclopentane in a weight ratio which produces the same vapor-pressure-verses-temperature curve as CFC-11.

TABLE X (THERMOSETTING FOAM EXAMPLES 16–17)

| COMPONENT, pbw | Ex. 16 | Ex. 17 |
|---|---|---|
| Stepan 2352 | 51.00 | 51.0 |
| Voranol 280 | 49.00 | 49.0 |
| Fyrol PCF | 15.0 | 15.0 |
| Dabco K-15 | 4.5 | 2.0 |
| Prop. Carb. | 5.0 | 5.0 |
| Texaco NP95 | 5.0 | 5.0 |
| OSI-51000 | 2.47 | 2.47 |
| PM-DETA | 0.25 | 0.15 |
| Water | 0.379 | 0.379 |
| SYNCP | 21.72 | 21.72 |
| TOTAL B-SIDE | 154.3 | 151.72 |
| PMDI | 213.10 | 104.0 |
| DC-5098 | 0.53 | 0.53 |
| SYNCP | 10.66 | 5.2 |
| TOTAL A-SIDE | 224.29 | 109.73 |
| TOTAL FOAM | 378.60 | 261.45 |
| Foam Index | 3.0 | 1.5 |
| Flame Spread Index | >75 | >450 |

TABLE XI (FOAMABLE BLEND EXAMPLES 23A–23F)

| Chemicals | Pbw |
|---|---|
| Stepan PS-2502A | 100.0 |
| Flame Retardant | 15.0 |
| Propylene Carbonate | 5.0 |
| Texaco NP-95 | 5.0 |
| Dabco K-15 | 3.2 |
| Tertiary Amine | 0.1 |
| Silicone Surfactant | 2.6 |
| Pentane | 23.5 |

TABLE XII

BROOKFIELD VISCOSITY AT 65° F.

| Example | Flame Retardant | SYNCP | EXTRCP |
|---|---|---|---|
| 23A | Fyrol PCF | 1184 | 1784* |
| 23B | Fyrol DMMP | 644 | 1040* |
| 23C | Fyrol CEF | 1564 | 2712* |
| 23D | Fyrol-6 | 1520 | 2296* |
| 23E | Fyrol-PBR | 1680 | 1940 |
| 23F | Fyrol-2 | 1540 | 2092* |

In TABLE XII, an asterisk (*) indicates an unstable (e.g., separated) mixture.

The amount of liquid flame retardant should be in the range of 5–30 pphp (parts per hundred polyol), and preferably is in the range of 10–20 pphp.

The preferred levels of propylene carbonate utilized are in the range of 5.00 pphp to 15.0 pphp, with the most preferred embodiment being 7.5 to 10.0 pphp. The preferred range of organic non-ionic surfactant utilized is between 0.0 and 10.0 pphp, with the most preferred embodiment being from 5.0 to 10.00 pphp. It was discovered that an equal weight ratio of propylene carbonate to non-ionic organic surfactant was the optimum balance of these different types of diluent.

As understood by those skilled in the art, the term "Index" as employed herein refers to the ratio of isocyanate functional groups to polyol functional.

While the invention has been particularly shown and described with reference to the preferred embodiments thereof, it will be understood by those skilled in the art that various alterations in-form and detail may be made therein without departing from the spirit and scope of the invention.

What is claimed is:

1. A composition for preparing a rigid thermosetting plastic polyester polyol-based foam, the composition comprising:
   a. polyester polyol;
   b. a polyisocyanate;
   c. a potassium catalyst;
   d. a tertiary amine catalyst; and
   e. a blowing agent comprising cyclopentane as an insulating gas inside closed cells, wherein the cyclopentane contains less than 22 percent impurities; and
   wherein the cyclopentane is miscible with the polyester polyol without a surfactant or an emulsifier.

2. The composition of claim 1, wherein the cyclopentane ranges from about 13 percent to about 30 percent of the composition.

3. A composition for preparing a rigid thermosetting plastic polyester polyol-based foam, the composition comprising:
   a. a blowing agent comprising cyclopentane as an insulating gas inside closed cells, wherein the cyclopentane contains less than 22 percent impurities; and
   b. a polar organic blowing agent capable of azeotroping with the cyclopentane.

4. The composition of claim 3 further comprising a viscosity depressant.

5. The composition of claim 3 further comprising a non-ionic surfactant.

6. A composition for preparing a rigid thermosetting plastic polyester polyol-based foam, the composition comprising:
   a blowing agent comprising cyclopentane as an insulating gas inside closed cells, wherein the cyclopentane contains less than 22 percent impurities; and
   wherein said composition has a Brookfield viscosity less than a composition having cyclopentane containing greater than 22 percent impurities.

7. The composition of claim 6 wherein the impurities are hexane isomers and n-pentane.

8. The composition of claim 6 wherein the synthetic cyclopentane is miscible with the polyester polyol without surfactants or an emulsifier.

* * * * *